(12) United States Patent
Perry et al.

(10) Patent No.: US 11,980,553 B2
(45) Date of Patent: May 14, 2024

(54) PROSTHETIC DEVICE

(71) Applicant: DEKA Products Limited Partnership, Manchester, NH (US)

(72) Inventors: N. Christopher Perry, Manchester, NH (US); Keith D. Violette, Sandown, NH (US); Grant A. Peret, Bedford, NH (US); David D. B. Cannan, Manchester, NH (US); Christopher C. Langenfeld, Nashua, NH (US); Jacob P. Laplante, Manchester, NH (US); Thomas A. Doyon, Manchester, NH (US)

(73) Assignee: DEKA Products Limited Partnership, Manchester, NH (US)

(*) Notice: Subject to any disclaimer, the term of this patent is extended or adjusted under 35 U.S.C. 154(b) by 164 days.

(21) Appl. No.: 17/338,727

(22) Filed: Jun. 4, 2021

(65) Prior Publication Data
US 2021/0401594 A1    Dec. 30, 2021

Related U.S. Application Data

(63) Continuation of application No. 15/870,162, filed on Jan. 12, 2018, now Pat. No. 11,026,816.

(60) Provisional application No. 62/445,549, filed on Jan. 12, 2017.

(51) Int. Cl.
| A61F 2/58 | (2006.01) |
| A61F 2/50 | (2006.01) |
| A61F 2/54 | (2006.01) |
| A61F 2/70 | (2006.01) |

(Continued)

(52) U.S. Cl.
CPC .................. *A61F 2/76* (2013.01); *A61F 2/50* (2013.01); *A61F 2/54* (2013.01); *A61F 2/586* (2013.01); *A61F 2/70* (2013.01); *A61F 2002/5072* (2013.01); *A61F 2002/6863* (2013.01);

(Continued)

(58) Field of Classification Search
CPC ...... A61F 2/76; A61F 2/50; A61F 2/54; A61F 2/586; A61F 2/70; A61F 2002/5072; A61F 2002/6863; A61F 2002/704; A61F 2002/7615; A61F 2002/7635
See application file for complete search history.

(56) References Cited

U.S. PATENT DOCUMENTS

| 6,896,704 B1 * | 5/2005 | Higuchi .................... A61F 2/70 623/64 |
| 8,979,943 B2 | 3/2015 | Evans et al. |
| 9,114,030 B2 | 8/2015 | van der Merwe et al. |

(Continued)

OTHER PUBLICATIONS

International Search Report and Written Opinion, dated Feb. 7, 2018, issued in PCT International Application No. PCT/US2018/013574, 13 pages.

(Continued)

*Primary Examiner* — Matthew J Lawson
*Assistant Examiner* — Aren Patel
(74) *Attorney, Agent, or Firm* — William A. Bonk, III

(57) ABSTRACT

A prosthetic device. The prosthetic device may include a flexure cut and/or a sensor to detect movement in accordance with a degree of movement. In an embodiment, the sensor may be disposed within the flexure cut. Other embodiments include at least one wire configured to connect a sensor located in a distal portion to a proximal portion, while annularly traversing a joint.

21 Claims, 20 Drawing Sheets

(51) Int. Cl.
*A61F 2/76* (2006.01)
*A61F 2/68* (2006.01)

(52) U.S. Cl.
CPC . *A61F 2002/704* (2013.01); *A61F 2002/7615* (2013.01); *A61F 2002/7635* (2013.01)

(56) References Cited

U.S. PATENT DOCUMENTS

| | | | |
|---|---|---|---|
| 2009/0143870 A1 | 6/2009 | Bedard et al. | |
| 2010/0191343 A1* | 7/2010 | Puchhammer | A61F 2/586 623/21.15 |
| 2010/0274365 A1* | 10/2010 | Evans | A61F 2/54 623/57 |
| 2014/0067083 A1 | 3/2014 | Wenstrand et al. | |
| 2015/0351935 A1* | 12/2015 | Donati | A61F 2/586 623/24 |
| 2016/0051383 A1 | 2/2016 | Goldfarb et al. | |

OTHER PUBLICATIONS

International Preliminary Report on Patentability, dated Jul. 16, 2019, issued in PCT International Application No. PCT/US2018/013574, 8 pages.
EP Communication pursuant to Rules 161(1) and 162 EPC, dated Sep. 4, 2019, issued in European Patent Application No. 18702851.9, 3 pages.

* cited by examiner

PROSTHETIC DEVICE

CROSS-REFERENCE TO RELATED APPLICATION(S)

This application is a Continuation of U.S. patent application Ser. No. 15/870,162, filed Jan. 12, 2018 and entitled RFID System and Method, now U.S. Pat. No. 11,026,816 issued Jun. 8, 2021, which claims the benefit of U.S. Provisional Application Ser. No. 62/445,549, filed Jan. 12, 2017 and entitled Prosthetic Device, which is hereby incorporated by reference in its entirety.

STATEMENT OF GOVERNMENT INTEREST

This invention was made with Government support under Contract Number HR0011-15-C-0125 awarded by DARPA. The Government has certain rights in the invention.

FIELD OF THE INVENTION

This disclosure relates to mechanical and medical devices. More specifically, this disclosure relates to prosthetics devices.

BACKGROUND

A prosthetic device provide functionality to a user that has lost a part of their body. Previous prosthetics continue to lack functionality desired by many users. Therefore, it has become desirable to improve prosthetics to facilitate increased benefits of the prosthetic device.

SUMMARY

In accordance with one implementation, a prosthetic device is disclosed. The prosthetic device includes a flexure cut; a sensor located in a distal portion of the prosthetic device to detect movement in accordance with a degree of movement wherein the sensor is disposed within the flexure cut; and at least one wire configured to connect the sensor to a proximal portion of the prosthetic device, wherein the at least one wire annularly traversing a joint of the prosthetic device.

Some embodiments of this aspect of the invention may include one or more of the following. Wherein the prosthetic device further including a finger structure, wherein the flexure cut is disposed within the finger structure. Wherein the finger structure comprising an outer surface, a first dissected surface and a second dissected surface that define the sides of the flexure cut, wherein the sides of the flexure cut extend linearly inward from an outer surface of the finger structure. Wherein the flexure cut traverses through the finger structure in a curvilinear manner. Wherein the sensor configured to measure movement in accordance with the at least one degree of degree. Wherein the prosthetic device further comprising a processor disposed in the proximal portion; and a joint configured for annual motion, the sensor disposed within the distal portion, wherein the at least one wire connecting the sensor in the distal portion to the processor in the proximal portion, wherein the at least one wire is configured to circumvent the joint without prohibiting annular motion.

In accordance with one implementation, a prosthetic device is disclosed. The prosthetic device includes a flexure cut configured to provide at least one degree of freedom to the prosthetic device.

Some embodiments of this aspect of the invention may include one or more of the following. Wherein the prosthetic device further includes a finger structure, wherein the flexure cut is disposed within the finger structure. Wherein the finger structure comprising an outer surface, a first dissected surface and a second dissected surface that define the sides of the flexure cut, wherein the sides of the flexure cut extend linearly inward from an outer surface of the finger structure. Wherein the flexure cut traverses through the finger structure in a curvilinear manner.

Wherein the prosthetic device further comprising a sensor disposed within the flexure cut, the sensor configured to measure movement in accordance with the at least one degree of degree. Wherein the prosthetic device further comprising a proximal portion; a distal portion; a processor disposed in the proximal portion; a joint configured for annual motion, the sensor disposed within the distal portion, and at least one wire connecting the sensor in the distal portion to the processor in the proximal portion, wherein the at least one wire is configured to circumvent the joint without prohibiting annular motion.

In accordance with one implementation, a prosthetic device is disclosed. The prosthetic device includes a proximal portion; a distal portion; a joint configured for annular motion; and at least one wire connecting the proximal portion to the distal portion, wherein the at least one wire is configured to circumvent the joint without prohibiting annular motion.

Some embodiments of this aspect of the invention may include one or more of the following. Wherein the at least one is configured to annularly traverse the joint in a first direction before annularly traversing the joint in a second direction. Wherein the prosthetic device further comprising a wire path disposed within the joint.

In accordance with one implementation, a prosthetic device is disclosed. The prosthetic device including a sensor configured to measure movement in accordance with at least one degree of freedom of the prosthetic device.

Some embodiments of this aspect of the invention may include one or more of the following. Wherein the sensor is a force resisting sensor. Wherein the sensor is configured to detect flexure. Wherein the prosthetic device further comprising a proximal portion, a distal portion, a joint configured for annular motion, the sensor disposed within the distal portion, and at least one wire connecting the sensor in the distal portion to the portion, wherein the at least one wire is configured to circumvent the joint without prohibiting annular motion.

In accordance with one implementation, a prosthetic device is disclosed. The prosthetic device comprising a flexure cut configured to provide at least one degree of freedom to the prosthetic device.

In accordance with one implementation, a prosthetic device is disclosed. The prosthetic device comprising a sensor configured to measure movement in accordance with at least one degree of freedom of the prosthetic device.

In accordance with one implementation, a prosthetic device is disclosed. The prosthetic device comprising a proximal portion, a distal portion, a joint configured for annular motion, and at least one wire connecting the proximal portion to the distal portion, wherein the at least one wire is configured to circumvent the joint without prohibiting annular motion.

The details of one or more embodiments are set forth in the accompanying drawings and the description below. Other features and advantages will become apparent from the description, the drawings, and the claims.

BRIEF DESCRIPTION OF THE DRAWINGS

These and other aspects will become more apparent from the following detailed description of the various embodiments of the present disclosure with reference to the drawings wherein.

DETAILED DESCRIPTION OF THE EXEMPLARY EMBODIMENTS

The construction of a prosthetic device may be coordinated to streamline assembly and use, accommodate additional functionality, implement tactile sensors, and enable wiring configurations. Without coordination, the prosthetic device may not fully accommodate various features. This disclosure discusses various embodiments of a coordinated prosthetic device that facilitates assembly, use, functionality, sensors, and/or wiring.

Figure 1:
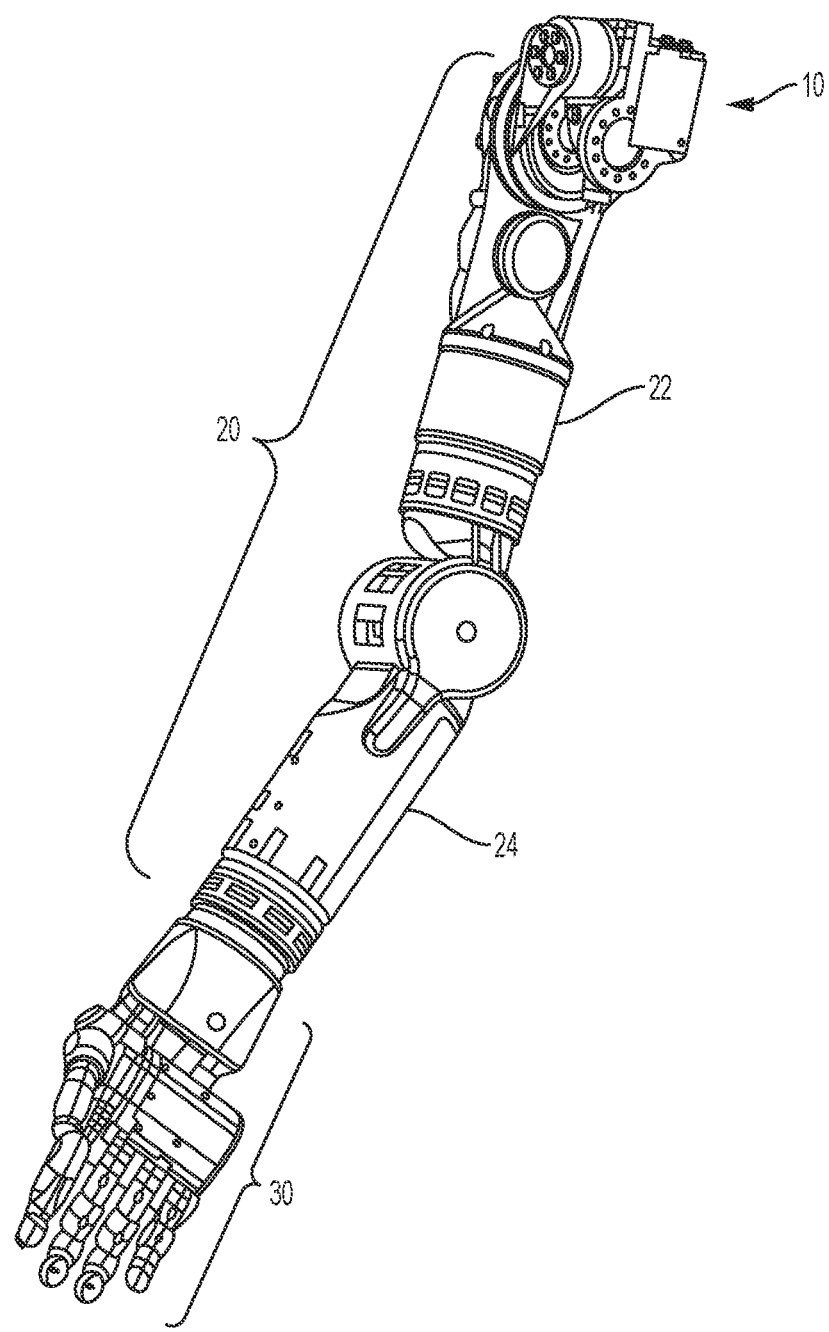
FIG. 1 is a perspective view of one embodiment of a prosthetic device.

Referring to FIG. 1, in some embodiments, a prosthetic apparatus 10 (which may also be referred to herein as a "prosthetic device") may include an arm assembly 20 and/or a hand assembly 30, for example, similar to any assemblies and/or prosthetic apparatus and/or device shown and/or described in U.S. application Ser. No. 13/088,085, filed Apr. 15, 2011, now U.S. Pat. No. 9,114,030, issued Aug. 25, 2015 and entitled System for Control of a Prosthetic Device. However, in some embodiments, the prosthetic apparatus may be a different apparatus and/or any prosthetic apparatus. The prosthetic apparatus 10 may be configured to move and articulate in a realistic manner to provide a user with effective and comfortable prosthetic use. For example, a component of the prosthetic apparatus 10, such as the arm assembly 20, may include a plurality of segments (e.g. a first segment 22 and a second segment 24) that provide a user with a desired number of degrees of freedom, including, but not limited to, those similar to human movement and function. In some embodiments, the number of degrees of freedom of the prosthetic apparatus 10 may be less than, equal to, or more than those provided by a human equivalent of the prosthetic apparatus 10.

In use, the arm assembly 20 may be coupled to one or more of a user's shoulder, a user's arm, a prosthetic shoulder assembly, and/or a prosthetic arm assembly. The length and structure of the arm assembly 20 may be modified as necessary to provide the user with a prosthetic-containing combination that has substantially the same length as a human arm. The prosthetic hand assembly 30 may be coupled to a user's arm, a user's wrist, a user's hand, a prosthetic arm, a prosthetic wrist, and/or a prosthetic hand. Either (or both) of the arm assembly 20 and hand assembly 30 may be controlled by a control system, which may be any control system including any one or more shown in U.S. application Ser. No. 13/088,063, filed Apr. 15, 2011, now U.S. Pat. No. 8,979,943, issued Mar. 17, 2015 and entitled Arm Prosthetic Device.

Figure 2:
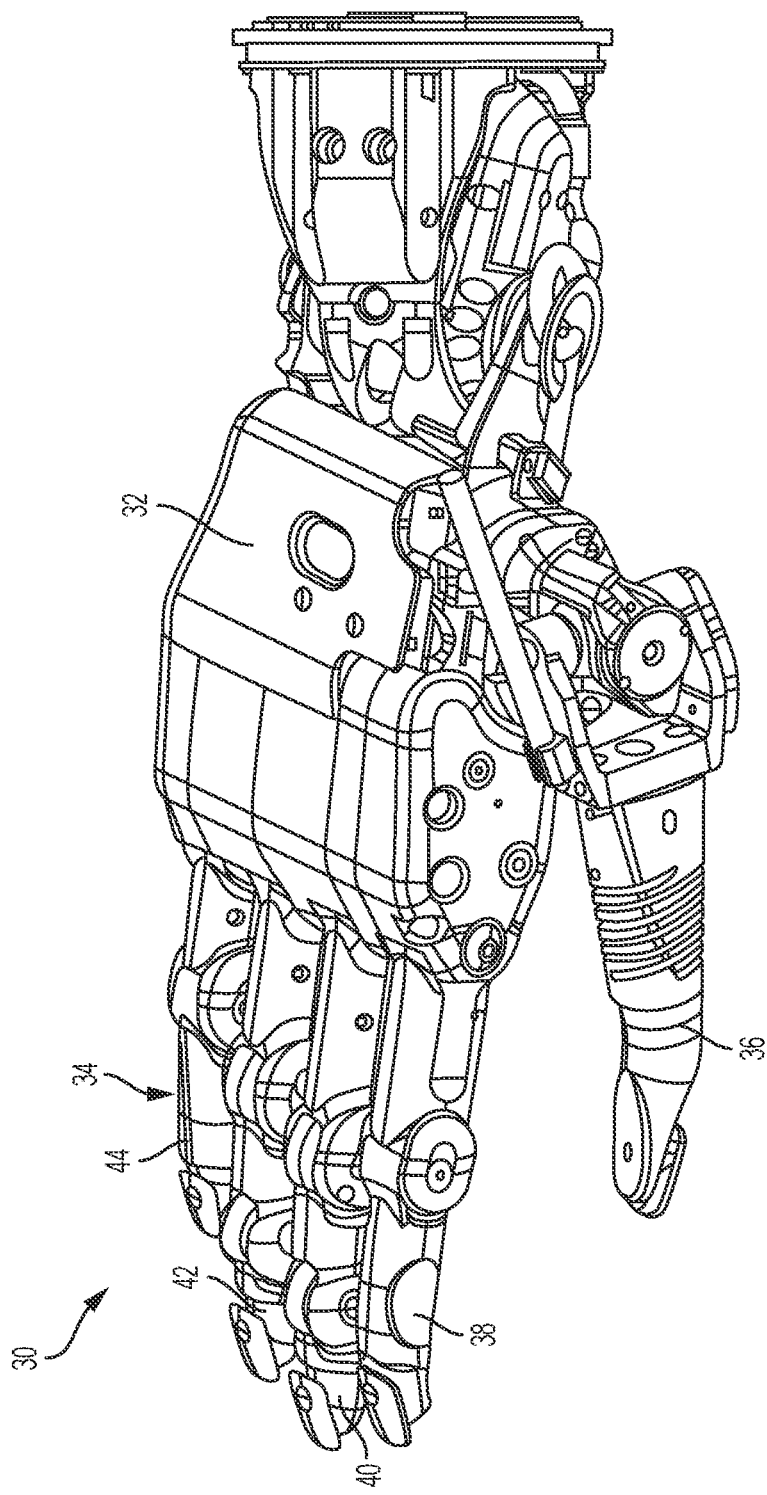
FIG. 2 is a perspective view of one embodiment of a hand assembly.

FIG. 2 depicts a perspective view of one embodiment of the hand assembly 30. The hand assembly 30 may include a palm structure 32 and/or at least one finger structure 34 that extends from the palm structure 32. The palm structure 32 may extend around the circumference of the hand assembly and may include both the underside and backside of the palm structure 32. The at least one finger structure 34 on the hand assembly 30 may be a thumb structure 36, an index structure 38, a middle structure 40, a ring structure 42 and/or a pinky structure 44.

Figure 3:
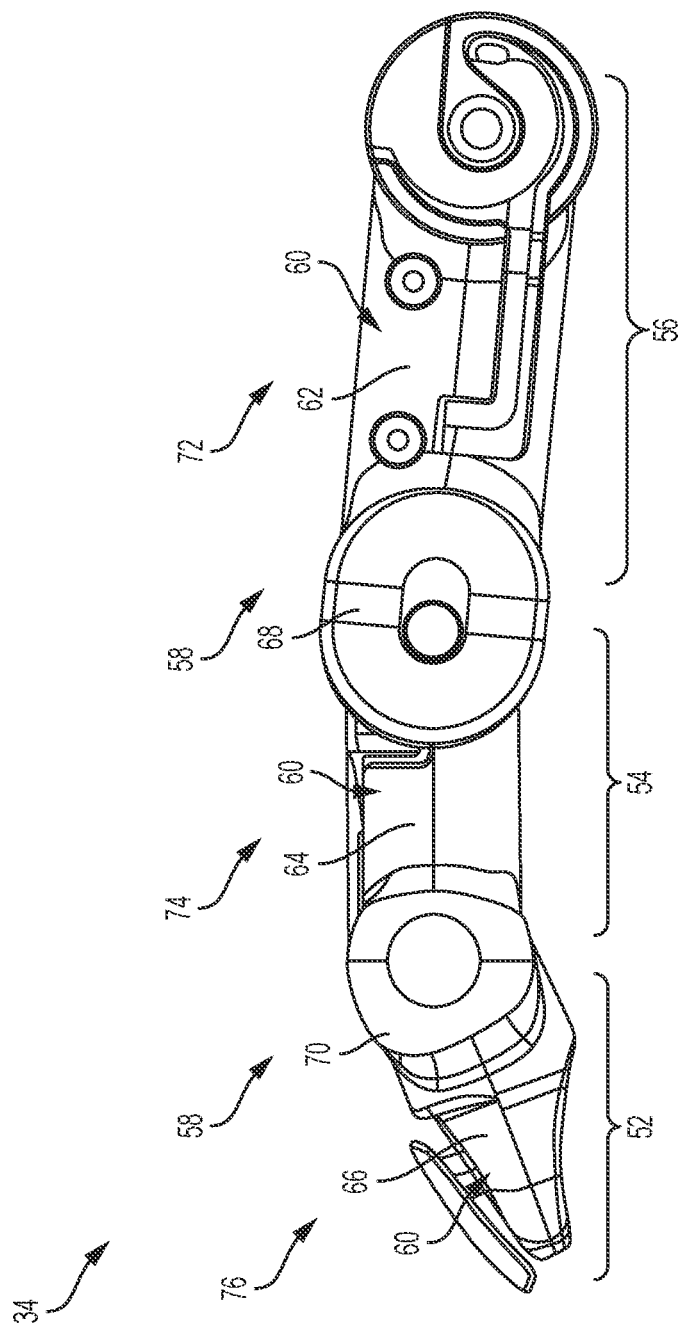
FIG. 3 is a side view of one embodiment of a finger structure.
Figure 4:
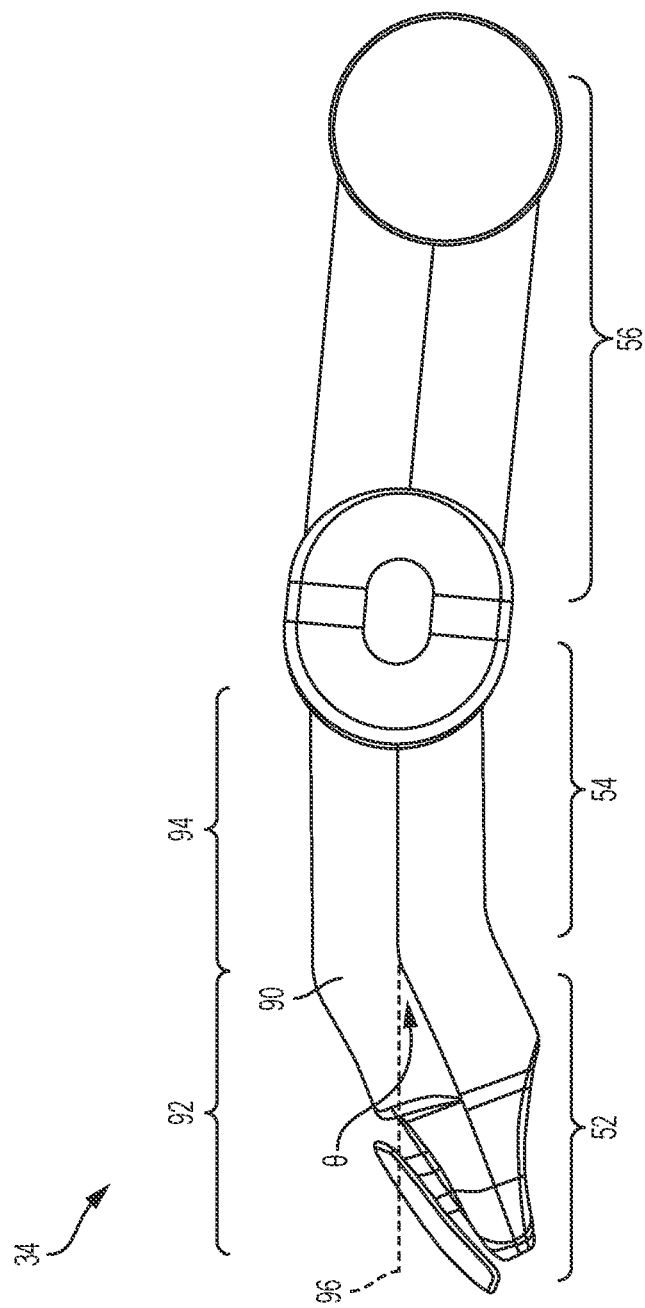
FIG. 4 is a side view of one embodiment of a finger structure.
Figure 5:
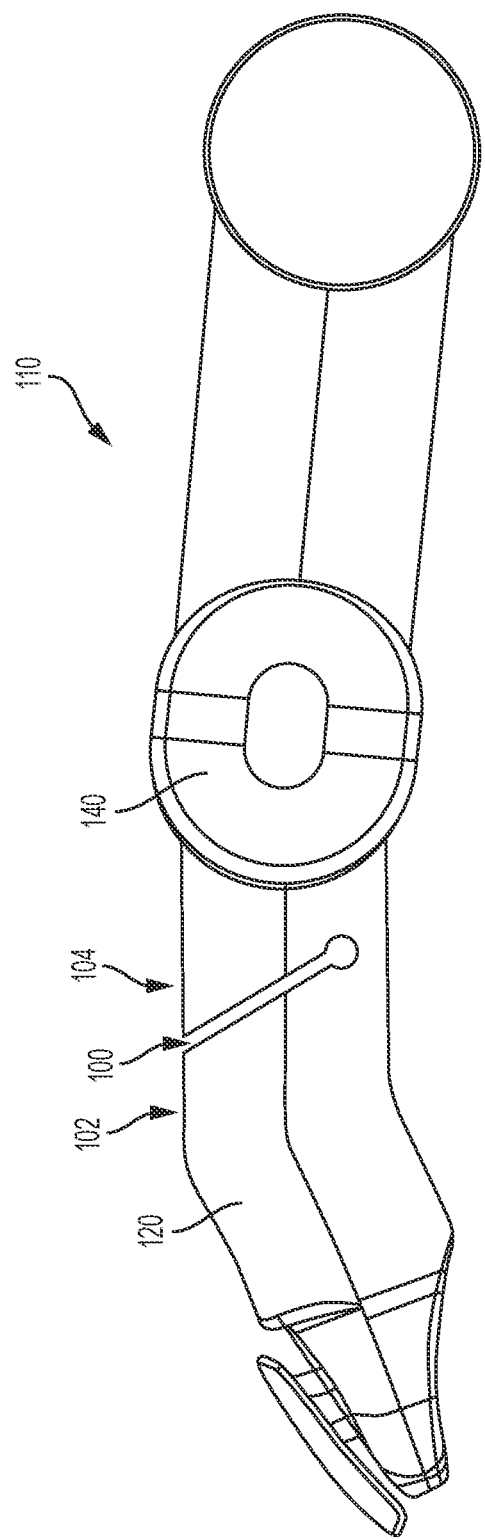
FIG. 5 is a side view of one embodiment of a finger structure.

As discussed above, the construction of the prosthetic apparatus 10 may be coordinated to accommodate assembly/use and functionality. FIGS. 3, 4, and 5 depict embodiments that utilize such coordinated construction to accommodate assembly, use, and functionality.

Referring now also to FIG. 3, the prosthetic apparatus 10 may include at least one finger structure 34. The finger structure 34 may have a distal portion 52, a middle portion 54, and a proximal portion 56. On some embodiments, at least one portion (e.g. the distal portion 52) may be configured to actuate or rotate about another portion (e.g. the middle portion 54). To facilitate such articulation, the finger structure 34 may include an articulating member 58 disposed between two portions (e.g. between the distal portion 52 and the middle portion 54 or between the middle portion 54 and the proximal portion 56).

In some embodiments, the finger structure 34 of the prosthetic apparatus 10 may include at least one phalange member 60 disposed in one or more of the portions 52, 54, and 56. One such embodiment may include three phalange members (e.g. first phalange member 62, second phalange member 64, and third phalange member 66) and one or more joints (e.g. first joint 68 and second joint 70) to facilitate movement of one or more of the phalange members 60. In some embodiments, the one or more of the joints (e.g. first joint 68 and/or second joint 70) may be toggled to form a locked angle between two phalange members 60, such that at least one of the phalange members 60 cannot articulate about a joint and/or another phalange member. Preventing articulation may be desirable/beneficial for many reasons, including, but not limited to, it decreases the available degrees of freedom but provides stability to the user.

One of the phalange members may be disposed closer to the point of user attachment than the other phalange members, and thusly referred to as the proximal phalange member 72. For example, in FIG. 3, the first phalange member 62 may also be referred to as proximal phalange member 72. Similarly, one of the phalange members may be disposed farther from the point of user attachment than the other phalange members (e.g. distal phalange member 76). A phalange member disposed between a distal phalange member and a proximal phalange member may be referred to as a middle phalange member (e.g. middle phalange member 74).

Referring now also to FIGS. 3 and 4, in some embodiments, each portion 52, 54, and 56 includes one and only one phalange member 60. By contrast, another embodiment of the finger structure 34 shown in FIG. 4 may include a phalange member (e.g. distal phalange member 90) that extends across more than one portion (e.g. across both the distal portion 52 and the middle portion 54). The distal phalange member 90 may appear to include two phalange members while formed monolithically without a joint therein. The monolithic phalange member may be configured to mimic the combined structure of a distal phalange member and a middle phalange member bent at a fixed angle in a fixed configuration. For example, in the embodiment shown in FIG. 4, the distal phalange member 90 may be monolithically formed such that a first portion 92 of the distal phalange member 90 and a second portion 94 appear to be bent from one another at a predetermined angle Θ (e.g. 25°) from reference line 96. Similar embodiments may include two portions bent at angle between approximately 20 degrees and approximately 30 degrees.

Figure 6:
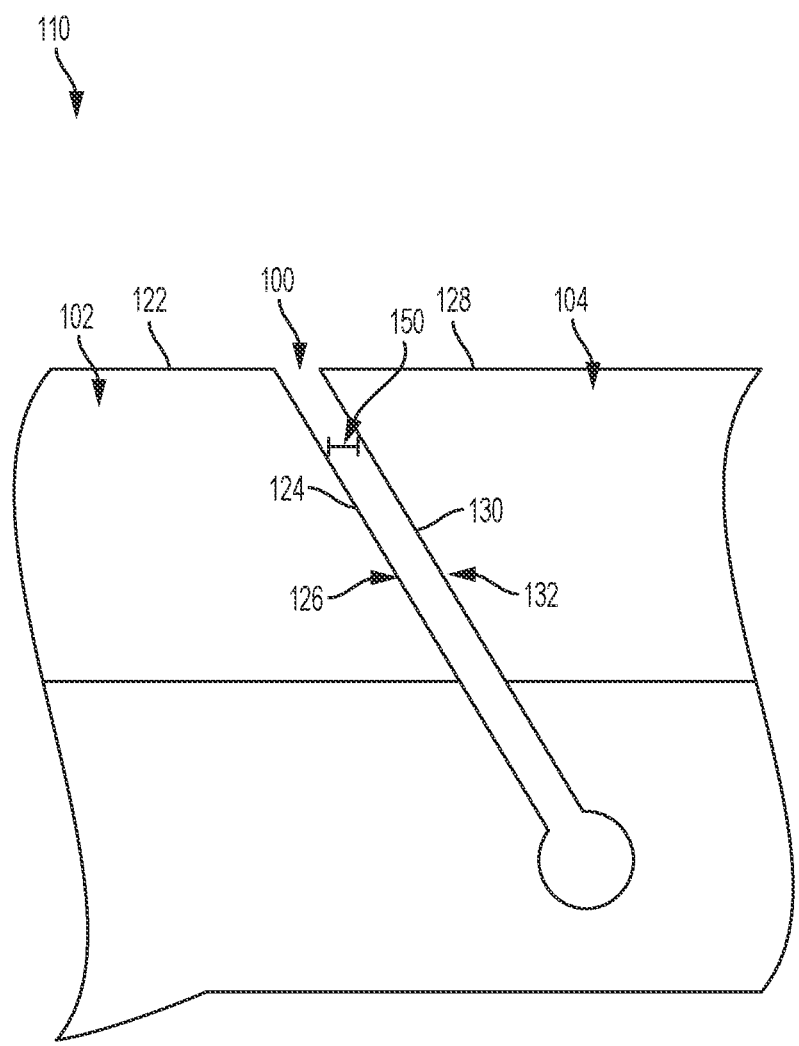
FIG. 6 is an enlarged view of a portion of FIG. 6.

Referring now also to FIG. 6, in some embodiments, the finger structure 110 may include a flexure cut 100. The flexure cut 100 may be disposed at least partially across and/or along a dimension of the finger structure 110. The flexure cut 100 may be formed by one of several manufacturing, molding, or machining processes. For example, the flexure cut 100 may be cut or machined from a fully-formed finger member. Some embodiments of the flexure cut 100 may utilize a slot, channel, void, gap, opening, aperture, recess, slit, orifice, and/or notch.

In various embodiments, a first dissected portion 102 and a second dissected portion 104 may define the boundaries of the flexure cut 100. In some embodiments, the dissected portions 102 and 104 may be, but need not be, proximal and distal of one another. For example, the dissected portions 102 and 104 may both be formed within a distal finger portion 120. Referring to the magnified view in FIG. 6, the first dissected portion 102 may have a first surface 122 and a second surface 124. The first surface 122 may extend generally transverse to the flexure cut 100 and the second surface 124 may extend generally along to the flexure cut, defining a first side 126 of the flexure cut 100. The second dissected portion 104 may similarly have a first surface 128 that may extend generally transverse to the flexure cut 100 and a second surface 128 that may extend generally along to flexure cut 100 to define a second side 132 of the flexure cut 100. Embodiments where more than two dissected portions that similarly define the boundaries of the flexure cut 100 are also within the scope of this disclosure.

In operation, the flexure cut 100 provides pivoting and/or spring functionality to portions of the finger member 110. For example, in an embodiment of the finger member 110 like FIG. 5 (having only a middle joint 140), a flexure cut 100 disposed within the distal finger portion 120 may provide pivoting flexure movement between the first dissected portion 102 and the second dissected portion 104. As pivoting occurs between the first dissected portion 102 and the second dissected portion 104, the width 150 of the flexure cut 100 may change (e.g. increase and/or decrease). The second surface 124 of the first dissected portion 102 and/or a the second surface 130 of the second dissected portion 104 may be configured to permit contact between the first dissected portion 102 and the second dissected portion 104. In an embodiment, such contact may be utilized to prevent overload and/or prevent flexure of the finger member 110 beyond a predetermined amount.

Figure 7:
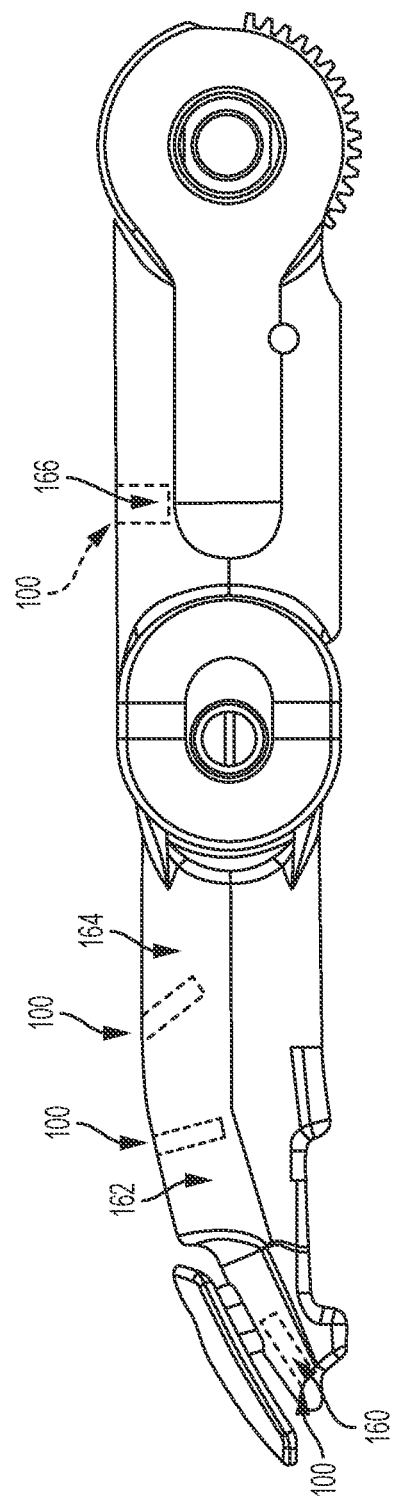
FIG. 7 is a side view of one embodiment of a finger structure.
Figure 8:
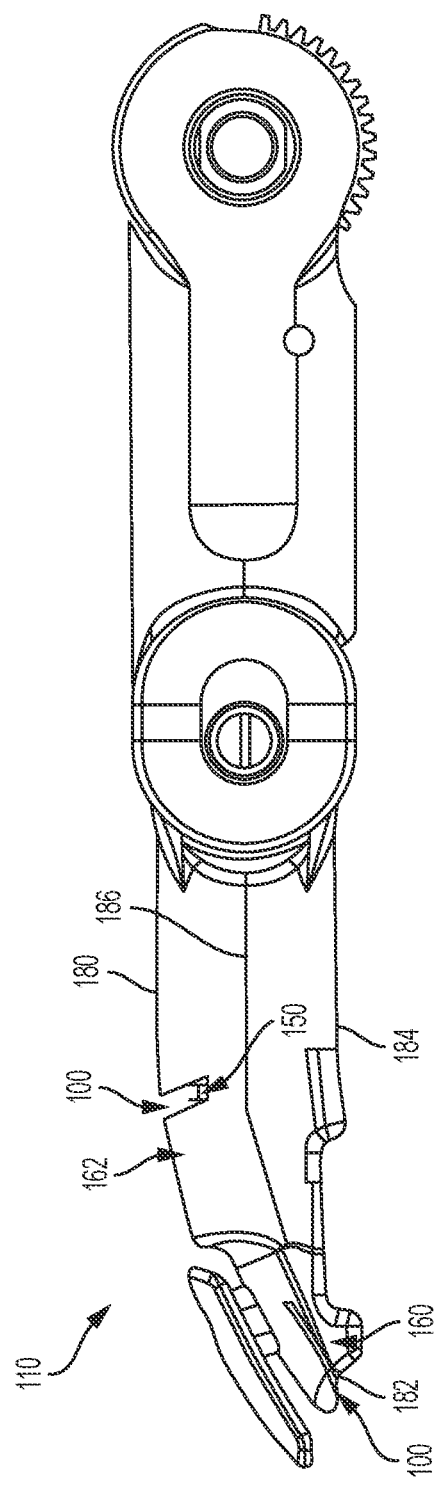
FIG. 8 is a side view of one embodiment of a finger structure.

Referring now also to FIG. 7, a flexure cut 100 may be positioned throughout the finger structure 110 in at least one of several regions 160, 162, 164, and/or 166. For example, the flexure cut 100 may be distally disposed in the fingertip region 160 or may be proximally disposed in the most proximal region 166. The flexure cut may be disposed in region 162 such that it provides some joint function to an otherwise joint-less distal portion 120 and middle portion 170. The flexure cut may also or instead be disposed in region 164, distal to a middle joint 172 or proximal joint 174 within the finger structure 110 and proximal to the fingertip region 150. One or more flexure cuts 100 may be located in an embodiment of the index structure 38. In an embodiment, one or more flexure cuts 100 may be located in more than one of the regions 160, 162, 164, and 166. For example, referring now also to FIG. 8, flexure cuts 100 may be located in both regions 160 and 162.

The orientation of the flexure cut 100 may be described generally by the originating surface (if applicable), the angle, and/or the direction of disposition. Referring again to FIG. 8, the flexure cut 100 may be embodied with a width 150 originating from the upper surface 180 of the finger structure 110. Similarly, the flexure cut 100 may originate from the fingertip surface 182, the bottom surface 184, and/or from a side surface 186 of the finger member 110. The finger structure 110 may include one or more flexure cuts 100 that travel in two or three dimensions within the finger structure.

The nature of flexure cut 100 may be described by its two-dimensional and three-dimensional geometry. For example, the flexure cut 100 may have a pyramidal, tubular, cylindrical, and spherical three-dimensional shape. The flexure cut 100 may have a triangular, rectangular, and/or circular two-dimensional surface (e.g. cross-section). A dimension (e.g. length) of the flexure cut 100 may extend in a linear and/or curvilinear manner. As shown in FIG. 5, the flexure cut 100 may be generally tubular or rectangular with a linear or curvilinear dimension.

Figure 9:
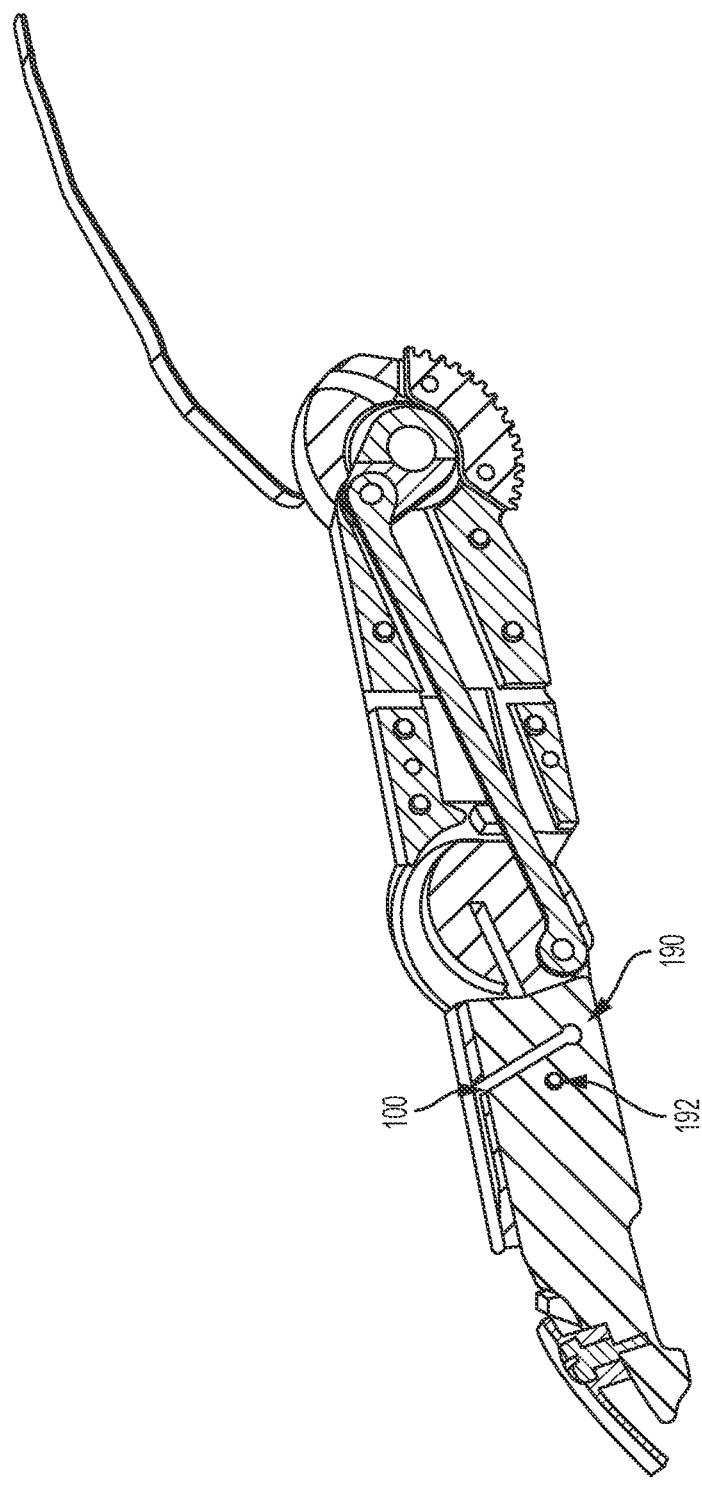
FIG. 9 is a perspective cross-section view of one embodiment of a finger structure.

The geometry of the flexure cut 100 may be configured to facilitate additional functionality. For example, the flexure cut 100 may include a stop feature 190. The stop feature 190 may be embodied as an additional component or may be created using the geometry of the flexure cut 100. For example, referring now also to FIG. 9, the curvilinear disposition of the flexure cut may be utilized as a stop feature to prevent overtravel. Similarly, extension of the flexure cut 100 to the exterior surface of the finger structure 110 (and surroundings thereof) may facilitate placement of a wedge 192 (see also FIG. 22) into the finger structure 110 to place a predetermined desired load on the flexure cut 100.

Generally, the prosthetic device 10 may be configured to provide tactile feedback, for example, by including one or more tactile sensors. For example, the prosthetic hand assembly 30 may include one or more sensors to provide tactile feedback and grip force sensitivity to the user. The prosthetic device 10 may be structurally accommodating to permit a desired type, number, and position of tactile sensors based on a variety of factors, including, but not limited to, desired function, spatial constraints, durability, calibration, speed, and hysteresis. While the below embodiments discuss the implementation of tactile sensor(s) with regards to particular portions of the prosthetic apparatus 10 (e.g. finger member 34), other components of the prosthetic apparatus 10 (e.g. the second segment 32) may similarly utilize the disclosed tactile sensor(s).

Figure 10:
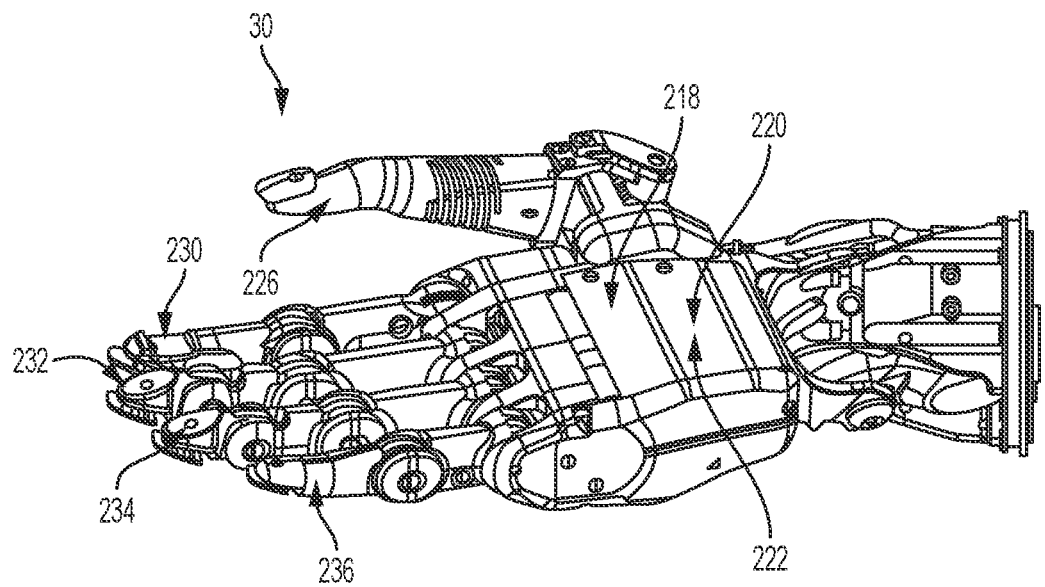
FIG. 10 is a perspective view of one embodiment of a hand assembly.
Figure 11:
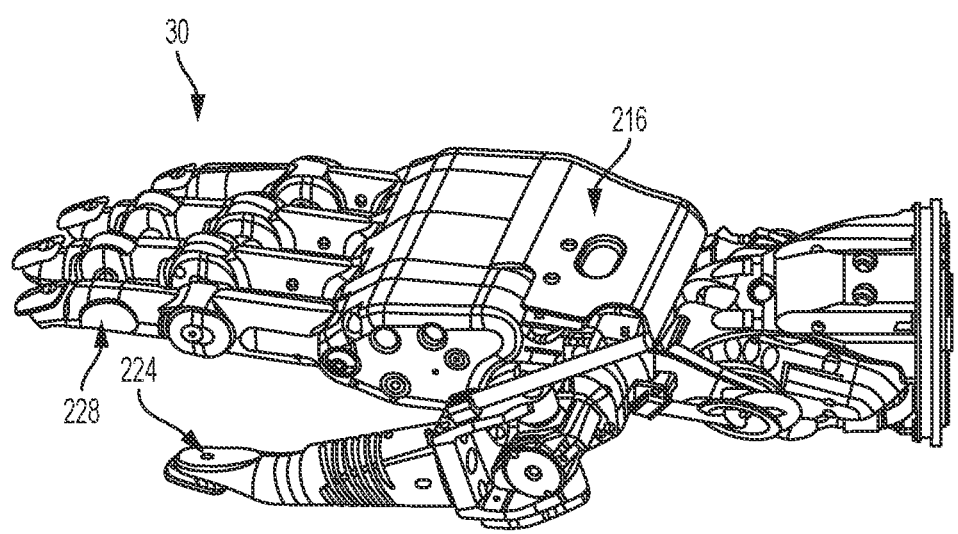
FIG. 11 is a perspective view of one embodiment of a hand assembly.

The structure of the prosthetic device 10 may be configured to permit placement of sensors in such a way as to prevent or limit shear forces and increase durability. The structure of the prosthetic device may also or instead be configured to accommodate calibration of the one or more sensor, to permit timely production of data, and to prevent hysteresis. Embodiments of the one or more tactile sensor discussed herein may include conductive cloth, a capacitive sensor, a strain gauge, a silicone/urethane sensor cube, a Hall Effect sensor, and/or a force sensing resistor. At least one component of the prosthetic device 10 (e.g. hand assembly 30 or finger member 34) may be configured to provide sufficient spatial consideration for the placement of one or more tactile sensor. Referring now also to FIGS. 10 and 11, the hand assembly 30 may be configured to dispose four sensors of a first type of sensor, each in one of four zones 216, 218, 220, 222. The hand assembly 30 may be configured to dispose seven sensors of a second type, each in one of seven zones 224, 226, 228, 230, 232, 234, 236. Embodiments of the hand assembly 30 may include the sensor(s) located on the exterior surface of the prosthetic device 10 and/or may be internal thereto, such that they provide tactile feedback related to the zone in which they are disposed. The finger structure 34 may be configured to include one or more tactile sensors disposed on the surface of the finger structure and/or within the interior of the finger structure (e.g. within an interior cavity). For example, the contour of the finger structure 34 may be modified to permit placement of an external tactile sensor within the working envelope of the finger structure 34. The finger structure 34 may be configured with at least a partially hollowed interior cavity within which one or more tactile sensors may be placed.

Referring now also to FIG. 10, an embodiment of a tactile sensor in zones 218, 220, and 222 may be a capacitive sensor. The hand assembly 30 may utilize signals from three areas (e.g. zones 218, 220 and 222) with capacitive sensors to assist with location identification of a tactile input. The respective outputs from the three areas may be compared using a processor to estimate the location of a tactile input.

Figure 12:
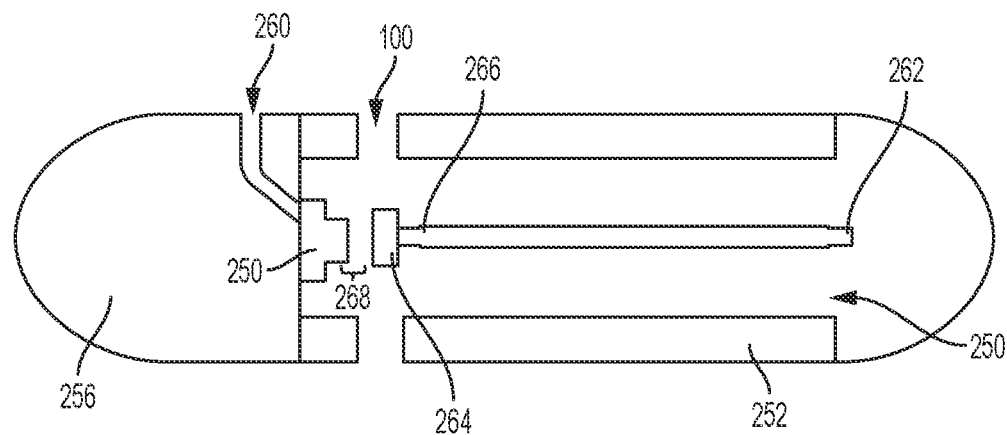
FIG. 12 is a schematic diagram of an embodiment of a finger structure.

As discussed above and now with reference also to FIGS. 12 and 13, the finger structure 34 may include at least one flexure cut 100 and a central bore 250 defined by the finger base 252. The finger member may further include a hall effect sensor 254 disposed within the central bore 250 and coupled to finger tip portion 256. The fingertip portion 256 may be configured to pivot (e.g. in the direction of 258) and may include a wire channel 260 to route wiring from the Hall Effect sensor 254 to a circuit (not shown). A magnet shaft 262, having a magnet 264 disposed at one end 266, may also be disposed within and extend along the length of the central bore 250. The magnet shaft 262 may be positioned such that a gap 268 is present between the magnet 264 and the Hall Effect sensor 254. In some embodiments, the magnet shaft 262 may be rotatably or longitudinal actuated (e.g. as a screw) to enable adjustment of the gap 268 between the magnet 264 and the Hall Effect sensor 254.

Figure 13:
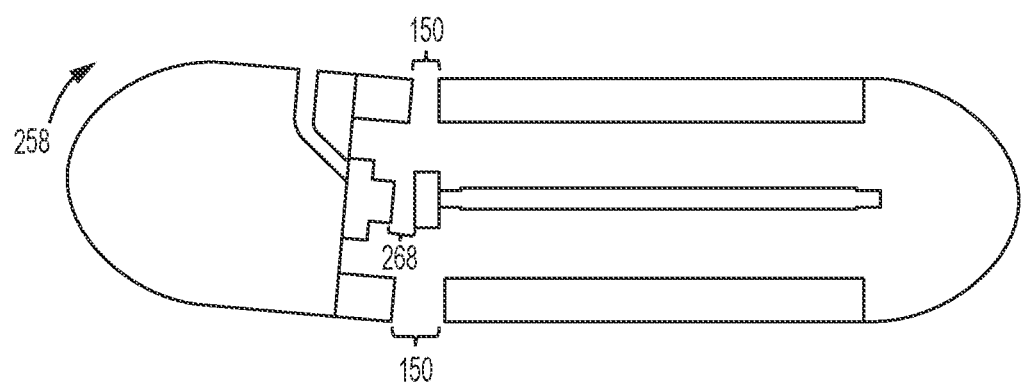
FIG. 13 is a schematic diagram of an embodiment of a finger structure.

In operation, the finger tip may pivot as a load is applied, as shown in FIG. 13. As the finger tip portion 256 pivots, the width 150 of flexure cut 100 in the direction of the pivoting may decrease as the width 150 of flexure cut 100 on the side opposite of the pivoting may increase. As the finger tip portion 256 pivots, the Hall Effect sensor 254 coupled thereto also pivots, changing the displacement of the gap 268 between the magnet 264 and the Hall Effect sensor 254. The Hall Effect sensor 254 may be configured to detect the change in displacement of the gap 268, which may correspond to an applied load and may be used to monitor the pivoting of the finger tip portion 256. The Hall Effect sensor 254 may be disposed at the juncture of two of the portions 52, 54, and 54 to ensure maximum sensing of the pivoting of the fingertip portion 256. Some embodiments may utilize a two dimensional Hall Effect sensor, while other embodiments may utilize a three dimensional Hall Effect sensor.

Figure 14:
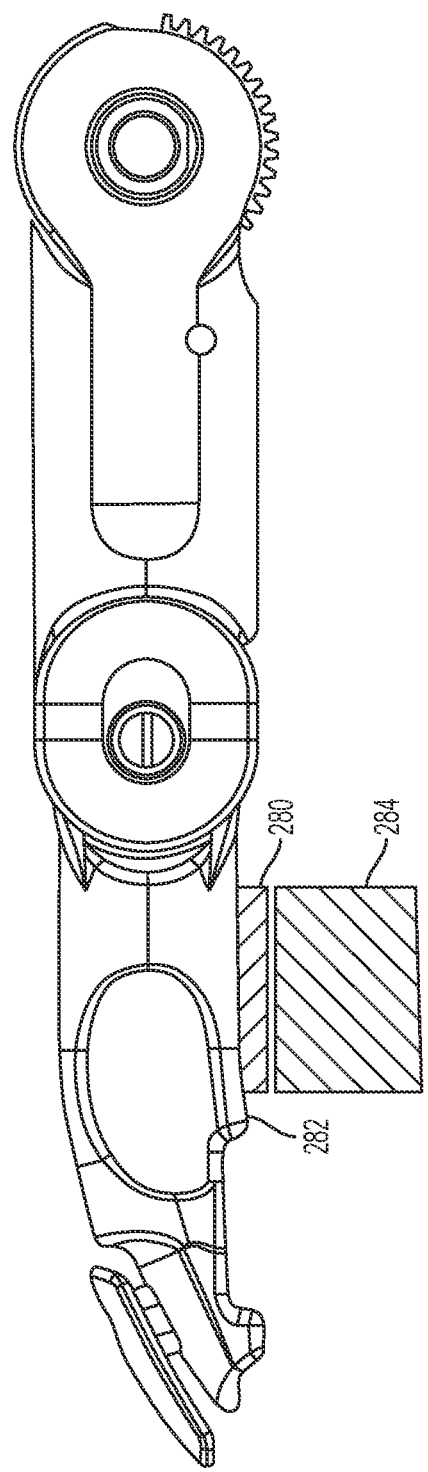
FIG. 14 is a side view of one embodiment of a finger structure.

In various embodiments, a force-sensing resistor ("FSR") may be included in the prosthetic apparatus 10 to provide tactile feedback and grip force sensitivity to the user. Referring now also to FIG. 14, an FSR 280 may be placed directly on an exterior surface 282 of a finger structure, without an intervening component between the FSR 280 and the contacting object 284. As a result, force may be directly detected by the FSR.

Figure 15:
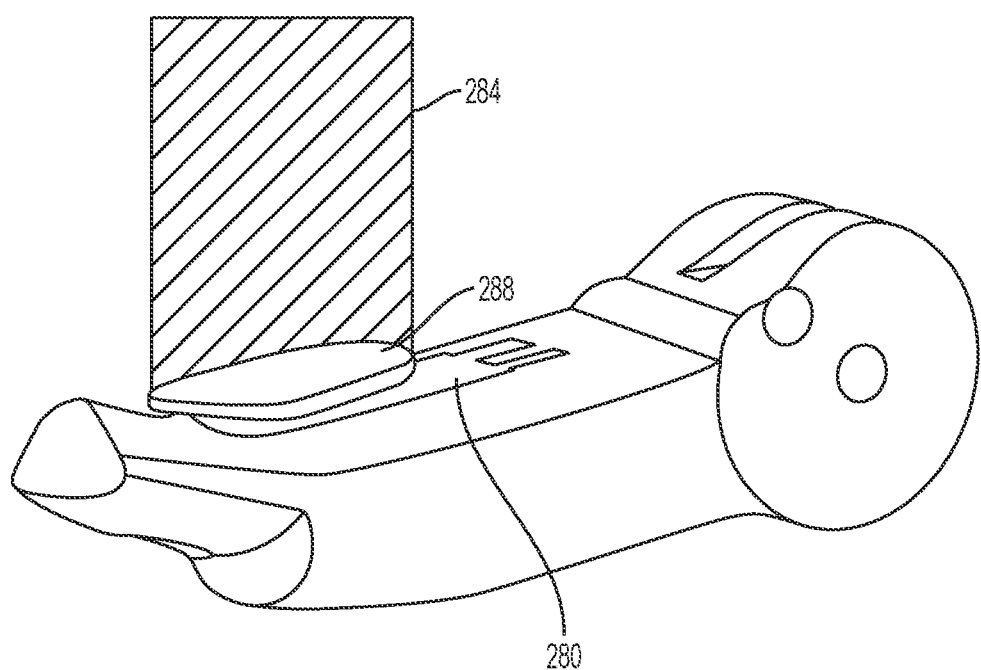
FIG. 15 is a perspective view of one embodiment of a finger structure.
Figure 16:
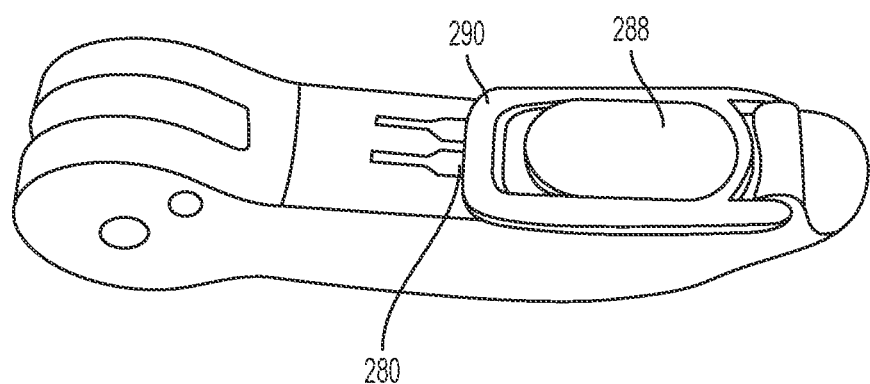
FIG. 16 is a perspective view of one embodiment of a finger structure.
Figure 17:
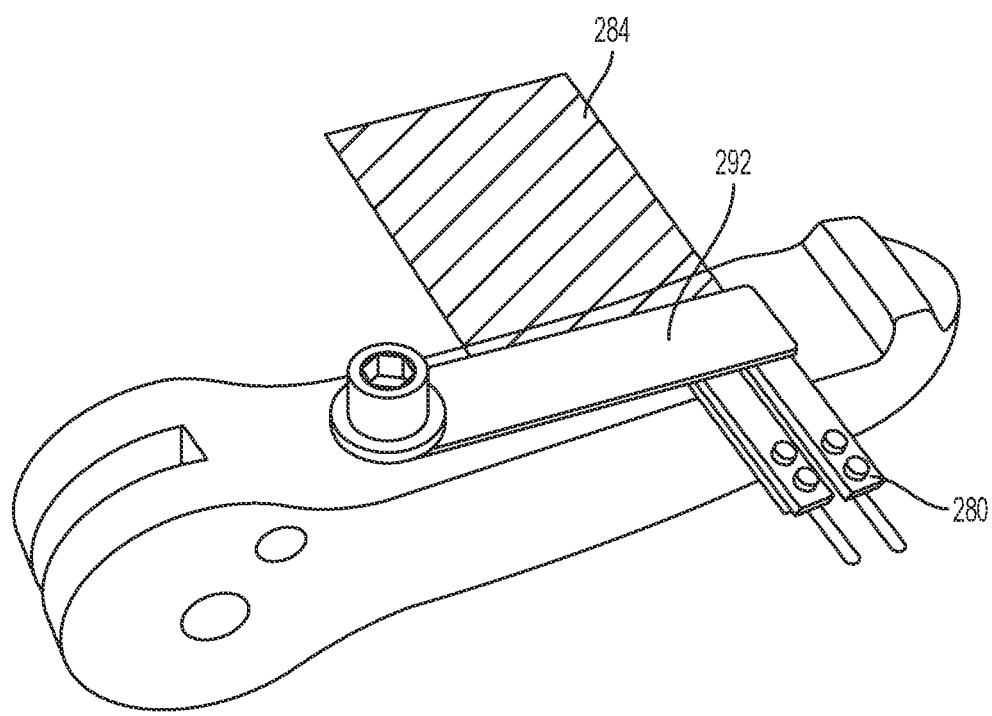
FIG. 17 is a perspective view of one embodiment of a finger structure.

Embodiments may include an FSR disposed on an exterior surface of a finger structure 110, with at least one intervening component 286 between the FSR 280 and the contacting object 284 to reduce shear force and/or increase the effective area of the FSR 280. For example, referring now also to FIG. 15, the finger structure 110 may further include an intervening component 286 (e.g. elastomer 288) disposed externally to the FSR 280, such that the elastomer 288 is disposed between a contacting object 284 and the FSR 280. Referring now also to FIG. 16, an embodiment may further include a rigid anvil cap 290 surrounding the radial outer surfaces of the elastomer 288 to create a larger effective area. Referring now also to FIG. 17, another example may include a cantilevered beam 292 disposed in communication with an FSR 280, such that the beam 292 prevents shear loads on the FSR and creates a larger effective area. As the contacting object 284 contacts the cantilevered beam 292, the contact is indirectly transferred to the FSR 280, which may create an output signal therefrom for further analysis.

Figure 18:
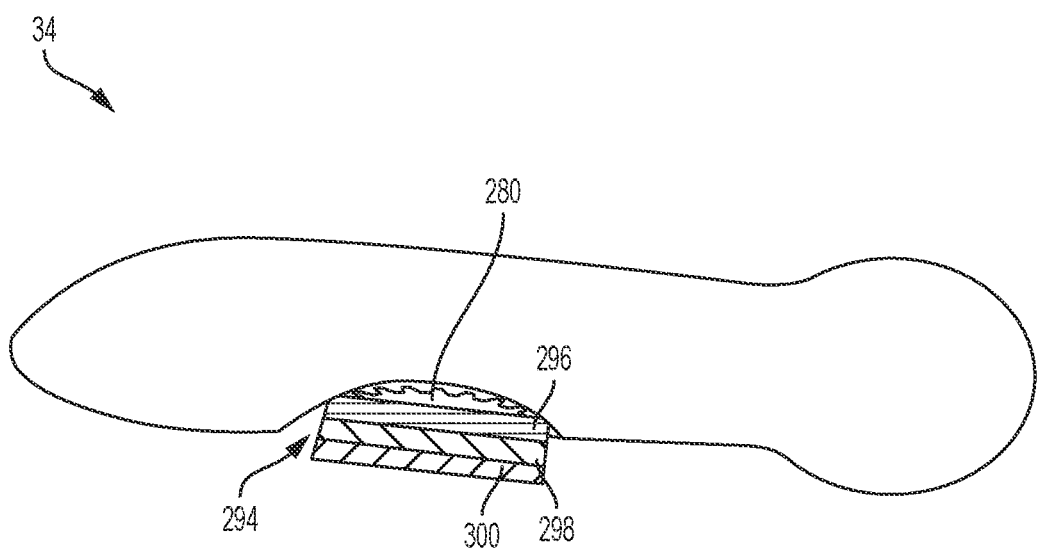
FIG. 18 is a side view of one embodiment of a finger structure.
Figure 19:
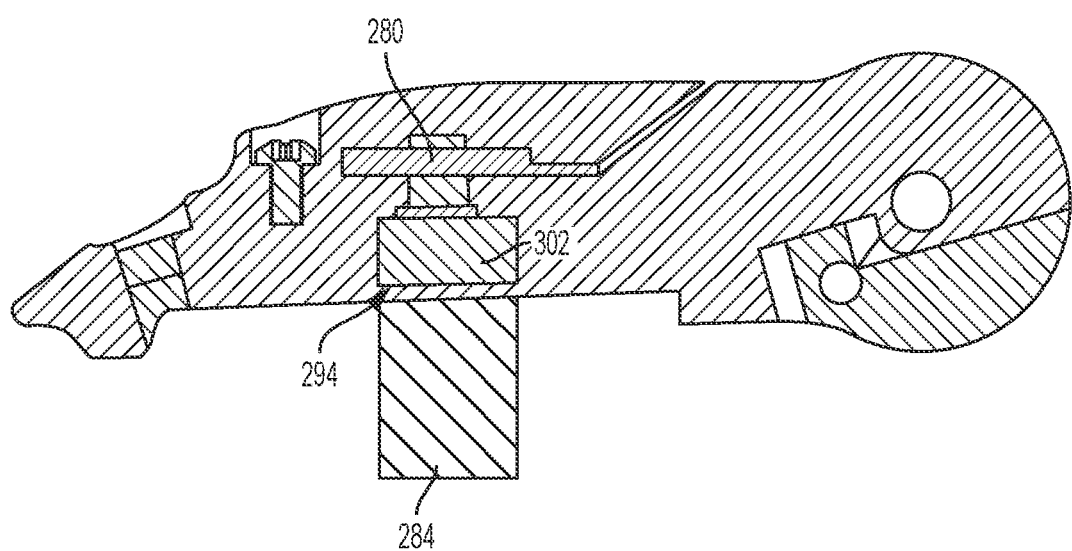
FIG. 19 is a side view of one embodiment of a finger structure.

Referring now also to FIG. 18, some embodiments of a finger structure 34 may include an at least partially hollow cavity 294 exposed to the surroundings of the finger structure 34. An FSR 280 may be disposed within the cavity 294. Various layers, including, for example, Teflon tape 296, silicone material 298, and steel 300 may be disposed externally to the FSR 280 to reduce shear force and increase the effective area. Referring now also to FIG. 19, another embodiment may include a finger member with a cavity 294, and an FSR 280 disposed within the cavity. The finger member may further include a linear actuator 302 configured to communicate with the FSR 280 through the finger member, to prevent shear and increase effective area. As a contacting object 284 contacts the actuator 302, it is actuated to contact the FSR 280. A Belleville spring may be used to preload the FSR 280, which prevents overload.

Figure 20:
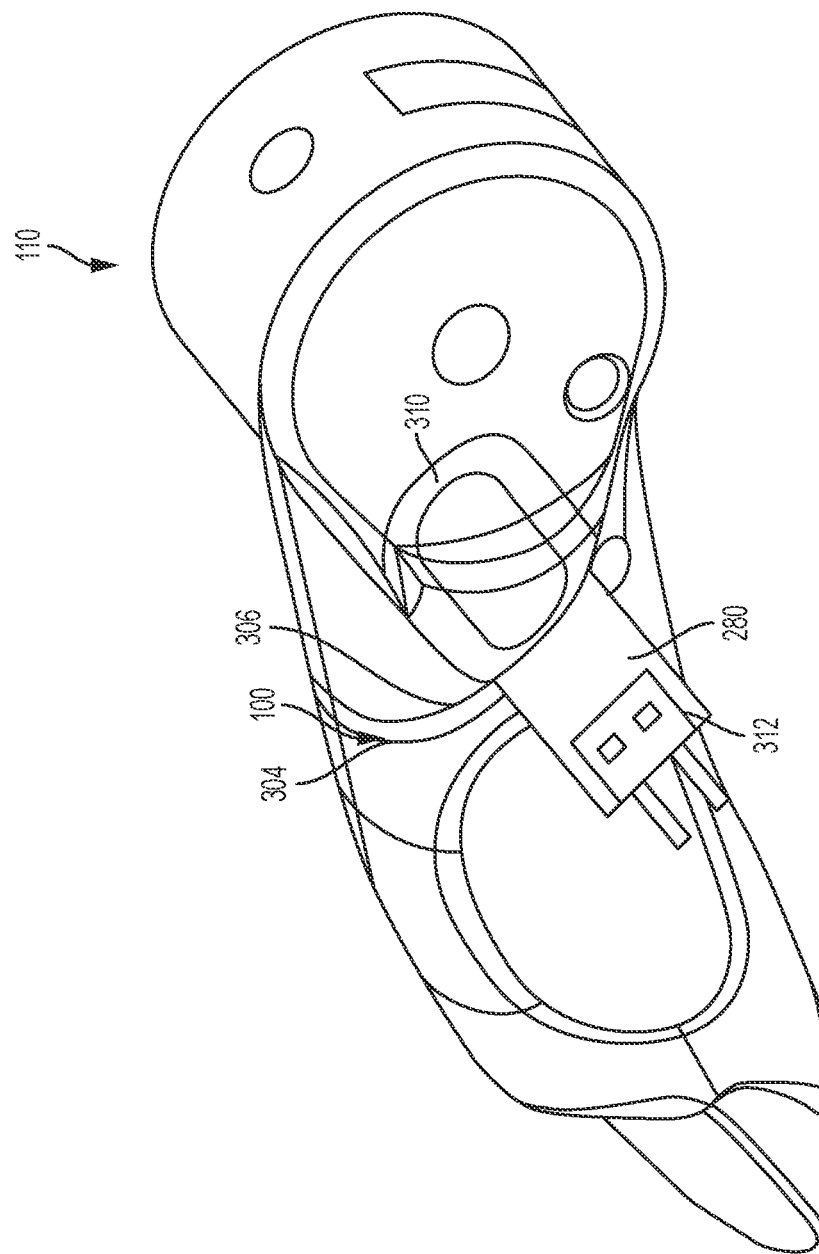
FIG. 20 is a perspective view of one embodiment of a finger structure.

As discussed above with reference to FIGS. 5 and 6, the finger structure 110 may include a flexure cut 100. Referring now also to FIG. 20, an FSR 280 may be disposed with the flexure cut 100. The FSR may be positioned within the gap such that the sensor is positioned between two dissected surfaces 304 and 306. The FSR 280 may be configured to sense a pressure as at least one of the dissected surfaces (304 or 306) approaches the other. In an embodiment, the FSR 280 may be configured to detect changes in the gap between the dissected surfaces.

To permit the FSR 280 to detect flexure enabled by the flexure cut 100, the FSR 280 may be coordinated in one of several configurations. In one such configuration, the distal end 310 of the FSR may be positioned within the flexure cut 100 and the proximal end 312 may be tapered proximally towards the user's hand/hand assembly.

Figure 21:
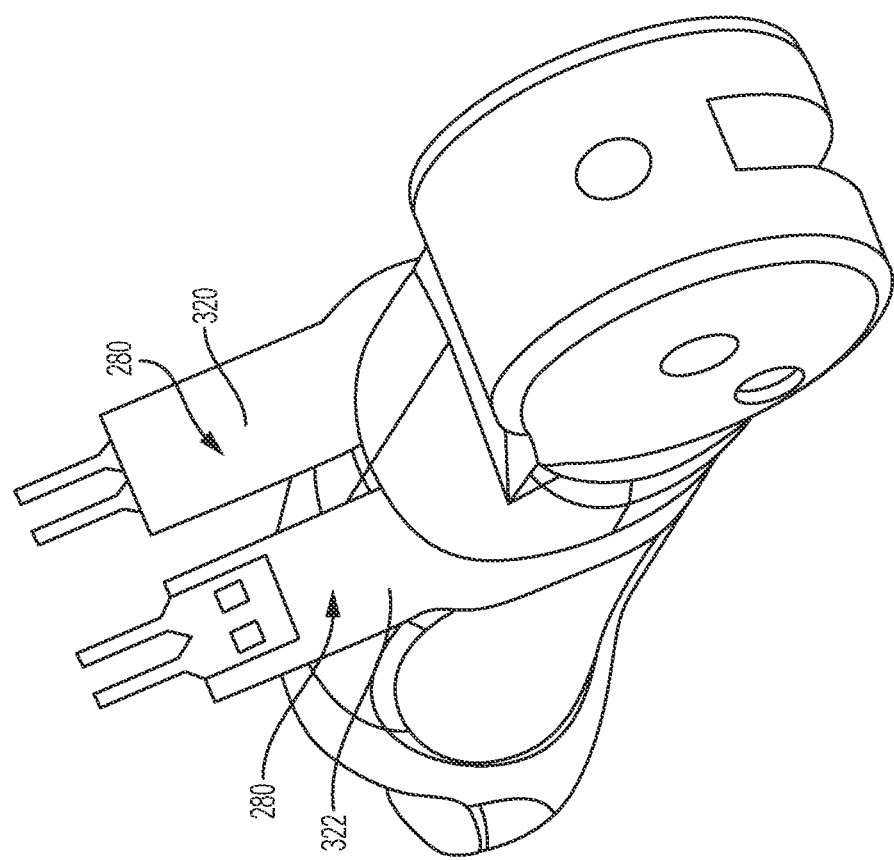
FIG. 21 is a perspective view of one embodiment of a finger structure.

Referring now also to FIG. 21, some embodiments may utilize more than one force sensing resistors (e.g. a first sensor 230 and a second sensor 322) disposed within the flexure cut 100. In such an embodiment, the distal ends of each of the force sensing resistors may be positioned within the flexure cut 100. As the finger flexes, FSR 320 and 322 each receive an input. Embodiments having more than one force sensing resistors may facilitate lateral comparative sensing. For example, the force sensed by the first force sensing resistor 320 may be compared to the force sensed by the second force sensing resistor 322. A processor and/or controller (not shown) may perform this comparison and produce an output indicative of the lateral force causing different sensed forces in the force sensing resistors.

Figure 22:
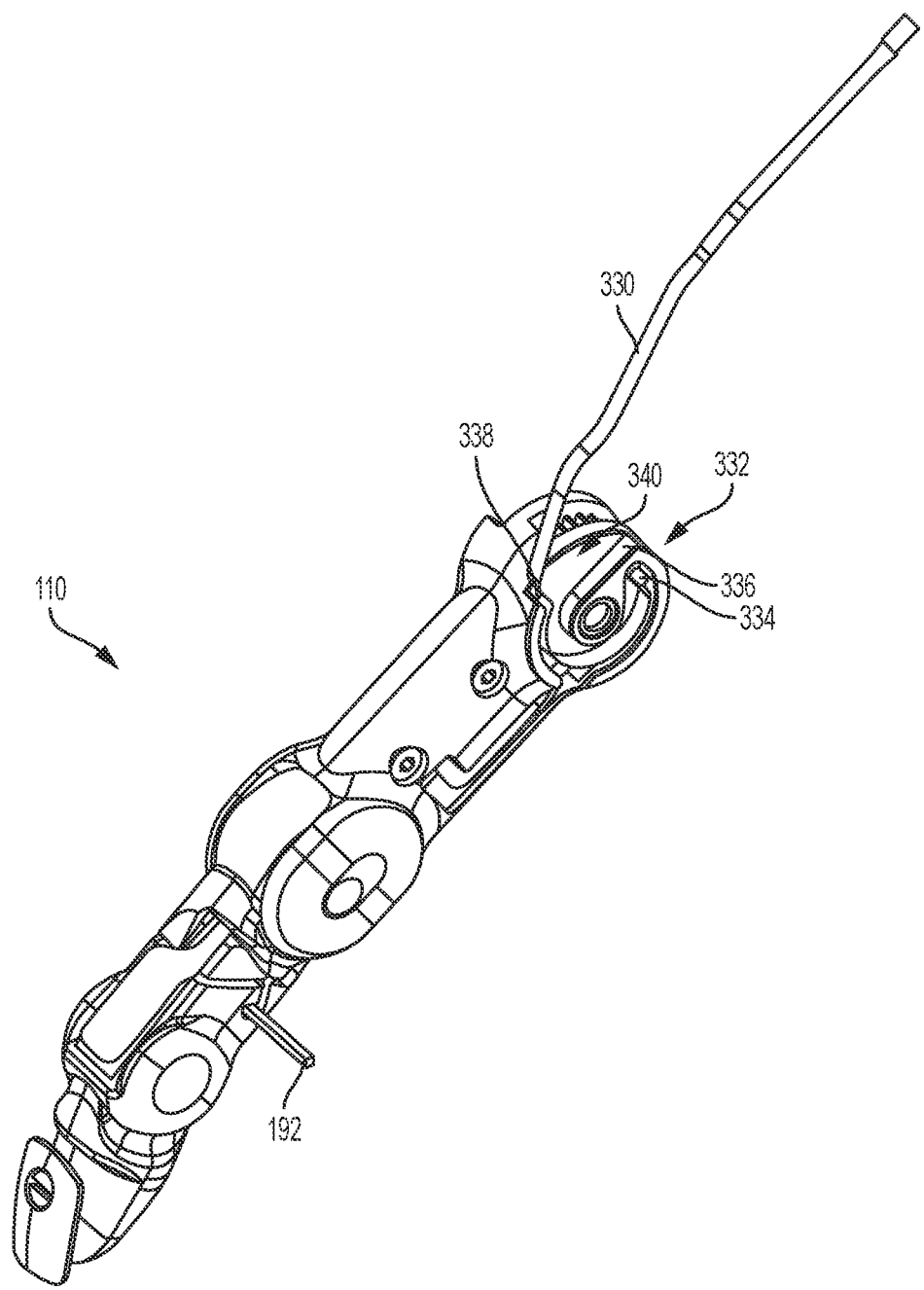
FIG. 22 is a perspective view of one embodiment of a finger structure.

As discussed below and now also with reference to FIG. 22, the construction of the prosthetic apparatus needs to be coordinated to transmit data and power to and from electrical components, particularly if wired communication is utilized. Although the electrical components need not be sensors, the embodiments below refer to the electrical component as a sensor for illustrate purposes. Embodiments utilizing other electrical components are within the scope of this disclosure.

Embodiments utilizing one or more of the above sensors may utilize wired or wireless components to transmit power to the sensor(s) and direct signals from the sensor(s). For example, the sensors may be powered by a wire that connects the sensor(s) to a power supply located outside of the finger member (e.g. in the hand assembly) and/or to a power supply within the finger member. In the event that wireless communication is not utilized to transmit data, the sensor(s) may be wired to a signal board to transmit signals from the finger member sensor(s) to another component (e.g. the hand assembly).

Embodiments utilizing wired components to transmit power and/or data signals must accommodate flexing joint (s) (e.g. finger joints) disposed along the wiring path, without compromising the integrity of the wire(s) utilized or affecting the flexing joint. Embodiments may utilize modified configuration(s) of the flexing joint(s) and/or wire(s) to achieve desired results. Embodiments may include a flexing joint configured to permit routing of wires therethrough. Some embodiments of the flexing joint may include a tension spring and/or torsion spring. A wiring channel may be disposed on, along, or within the flexing joint. Other embodiments may include non-wired components, such as a circuit board, radial brushers/wipers, axial brushes, and/or a laminated circuit board. In one such example shown in FIG. 22, the wiring cable 330 may be configured to permit joint flexure and wire routing.

The wire may be configured to first annularly traverse a first amount (e.g. 45 degrees) of a circular joint 332 in a first direction (e.g. counterclockwise) and second traverse the a second amount in a second direction (e.g. clockwise). Referring now also to FIG. 22, the wire may be configured to transition from traversing in the first direction to the second direction by traveling to and around a dowel 334. Thereafter, the wire may be configured to annularly traverse the remainder of the joint in the second direction. In an embodiment, the wire may be configured to travel to and around more than one dowel and in additional directions of travel. The finger structure 110 may be configured to facilitate the wiring travel. For example, the joint may include an inner annular surface 336, an outer annular surface 338, and a wire path 340 there between. As the joint flexes, the wire may be configured such that it remains around the dowel 334 but translates within the wire path 340 between the inner annular surface 336 and outer annular surface 338.

In a hand assembly 30 having more than one finger member 34, the finger members 34 may be analogous and/or different. For example, one finger member 34 (e.g. index structure) included in the hand assembly may have a monolithic phalange member with a fixed angle, while another finger member 34 may not. Some finger members 34 may utilize two joints, while others may utilize only one joint. Similarly, one finger member 34 (e.g. index structure) may include multiple flexure cuts 100 to facilitate sensing on multiple surfaces of the finger member 34, while other finger members 34 may not. In some instances, one finger member 34 may permit a particular sensor type and disposition, while others (e.g. pinky structure) may not do to their size or operation. In some instances, some finger structures (e.g. ring and middle finger) may be interchangeably utilized on a left or right hand assembly, while the construction of others necessitates mirrors that may only be used on either a left or right hand assembly. In some instances, phalanges may be interchangeable amongst several finger members (e.g. middle and ring structures only differ with the length of the proximal phalange utilized). These differences are not exhaustive and one skilled in the art shall appreciate that other different combinations are within the scope of this disclosure.

Various alternatives and modifications may be devised by those skilled in the art without departing from the disclosure. Accordingly, the present disclosure is intended to embrace all such alternatives, modifications and variances. Additionally, while several embodiments of the present disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. And, those skilled in the art will envision other modifications within the scope and spirit of the claims appended hereto. Other elements, steps, methods and techniques that are insubstantially different from those described above and/or in the appended claims are also intended to be within the scope of the disclosure.

The embodiments shown in drawings are presented only to demonstrate certain examples of the disclosure. And, the drawings described are only illustrative and are non-limiting. In the drawings, for illustrative purposes, the size of some of the elements may be exaggerated and not drawn to a particular scale. Additionally, elements shown within the drawings that have the same numbers may be identical elements or may be similar elements, depending on the context.

Where the term "comprising" is used in the present description and claims, it does not exclude other elements or steps. Where an indefinite or definite article is used when referring to a singular noun, e.g. "a" "an" or "the", this includes a plural of that noun unless something otherwise is specifically stated. Hence, the term "comprising" should not be interpreted as being restricted to the items listed thereafter; it does not exclude other elements or steps, and so the scope of the expression "a device comprising items A and B" should not be limited to devices consisting only of components A and B. This expression signifies that, with respect to the present disclosure, the only relevant components of the device are A and B.

Furthermore, the terms "first", "second", "third" and the like, whether used in the description or in the claims, are provided for distinguishing between similar elements and not necessarily for describing a sequential or chronological order. It is to be understood that the terms so used are interchangeable under appropriate circumstances (unless clearly disclosed otherwise) and that the embodiments of the disclosure described herein are capable of operation in other sequences and/or arrangements than are described or illustrated herein.

A number of embodiments have been described. Nevertheless, it will be understood that various modifications may be made. Accordingly, other embodiments are within the scope of the following claims.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention.

What is claimed is:

1. A prosthetic device comprising:
   a monolithic first portion defining a flexure cut having a first side and a second side and a gap between the first side and the second side;
   a second portion;
   a hinge connecting the first portion to the second portion;
   a sensor for measuring a change in dimension of the gap.

2. The prosthetic device of claim 1 wherein the sensor comprises a hall sensor.

3. The prosthetic device of claim 2 wherein the hall sensor is on the first side and the sensor further comprises a magnet on the second side.

4. The prosthetic device of claim 3 further comprising a wire connected to the sensor and traversing the first portion, the hinge and the second portion.

5. The prosthetic device of claim 4, wherein the wire is configured to annularly
   traverse the hinge in a first direction before annularly traversing the hinge in a second direction.

6. The prosthetic device of claim 4, further comprising a wire path for the wire disposed within the hinge.

7. The prosthetic device of claim 1 wherein the second portion is monolithic and defines a second a flexure cut having a first side and a second side and a second gap between the first side and the second side of the second flexure cut, the prosthetic device further comprising a second sensor for the measuring a change in dimension of the second gap.

8. The prosthetic device of claim 1, wherein the flexure cut traverses through the first portion in a curvilinear manner.

9. A prosthetic finger comprising:
   a monolithic distal member defining a flexure cut having a first side and a second side and a gap between the first side and the second side;
   a proximal member;
   a hinge connecting the proximal member to the distal member;
   a sensor in the distal member for measuring a change in dimension of the gap.

10. The prosthetic device of claim 9 wherein the sensor comprises a hall sensor.

11. The prosthetic device of claim 10 wherein the hall sensor is on the first side and the sensor further comprises a magnet on the second side.

12. The prosthetic device of claim 9 further comprising a wire connected to the sensor and traversing the distal member, the hinge and the proximal member.

13. The prosthetic device of claim 12, wherein the wire is configured to annularly
    traverse the hinge in a first direction before annularly traversing the hinge in a second direction.

14. The prosthetic device of claim 12, further comprising a wire path for the wire disposed within the hinge.

15. The prosthetic device of claim 9 wherein the proximal member is monolithic and defines a second a flexure cut having a first side and a second side and a second gap between the first side and the second side of the second flexure cut, the prosthetic device further comprising a second sensor for the measuring a change in dimension of the second gap.

16. The prosthetic device of claim 9, wherein the flexure traverses through the proximal member in a curvilinear manner.

17. The prosthetic device of claim 9 wherein the distal member has a first portion and a second portion, the first portion at an angle to the second portion.

18. The prosthetic device of claim 17 wherein the flexure cut is in the first portion and the first portion is attached to the hinge.

19. A method for detecting tactile feel with a prosthetic device, the method comprising:
    providing a monolithic prosthetic member having a flexure cut, the cut having a first and second side and defining a gap therebetween;
    applying a load to the prosthetic member to flex the flexure cut to change the gap;
    measuring the change in the gap.

20. The method of claim 19 further comprising:
    providing a hall sensor on the first side and a magnet on the second side for measuring the change in the gap.

21. The method of claim 19 wherein the applying the load includes decreasing the gap.

* * * * *